(12) United States Patent
Schawe et al.

(10) Patent No.: US 6,551,835 B1
(45) Date of Patent: Apr. 22, 2003

(54) METHOD AND APPARATUS FOR THERMALLY ANALYZING A MATERIAL

(75) Inventors: Jürgen Schawe, Volketswil (CH); Ingo Alig, Weiterstadt (DE); Dirk Lellinger, Weiterstadt (DE)

(73) Assignee: Mettler-Toledo GmbH, Greifensee (CH)

( * ) Notice: Subject to any disclaimer, the term of this patent is extended or adjusted under 35 U.S.C. 154(b) by 0 days.

(21) Appl. No.: 09/670,110

(22) Filed: Sep. 26, 2000

(30) Foreign Application Priority Data

Sep. 27, 1999 (EP) ............................................. 99118982

(51) Int. Cl.[7] ............................................... G01N 25/20
(52) U.S. Cl. ............................ 436/147; 374/10; 374/11
(58) Field of Search .......................... 436/147; 422/51, 422/109; 374/1, 10–13, 29, 43, 44

(56) References Cited

U.S. PATENT DOCUMENTS

| | | | | |
|---|---|---|---|---|
| 5,152,607 A | * | 10/1992 | Ibar ............................ | 374/45 |
| 5,224,775 A | * | 7/1993 | Reading et al. ............... | 374/11 |
| 5,549,387 A | * | 8/1996 | Schawe et al. ............... | 374/10 |
| 5,599,104 A | * | 2/1997 | Nakamura et al. ............ | 374/12 |
| 5,788,373 A | * | 8/1998 | Huetter et al. ................ | 374/10 |
| 6,007,240 A | * | 12/1999 | Price ............................ | 374/55 |

FOREIGN PATENT DOCUMENTS

| | | |
|---|---|---|
| EP | 0559362 | 9/1993 |
| EP | 0572164 | 12/1993 |
| EP | 0701122 | 3/1996 |
| WO | 9533199 | 12/1995 |
| WO | 9533200 | 12/1995 |
| WO | 9618886 | 6/1996 |

OTHER PUBLICATIONS

Schawe, J. "Investigations of the glass transitions of organic and inorganic substances. DSC and temperature–modulated DSC", J. Therm. Anal. (1996), 47(2), 475–484 (Abstract).*
Schawe, J. et al., "The analysis of temperature modulated DSC measurements by means of the linear response theory", Thermochim. Acta (1996), 287(2), 213–223.*
Schawe, J. "Principles for the interpretation of temperature-modulated DSC measurements. Part 2: A thermodynamic approach", Thermochimica Acta (1997), 304/305, 111–119 (Abstract).*
Schawe, J. et al. "Investigation of polymer melting by temperature modulated differential scanning calorimetry and its description using kinetic models", Thermochimica Acta (1997), 304/305, 179–186 (Abstract).*
Amengual A et al: Systeme D'Analyse Thermique et D'Analyse Calorimettrique Differentielle (DSC): Bristol, vol. 22, No. 7, Jul. 1989, pp. 433–437.

* cited by examiner

Primary Examiner—Jill Warden
Assistant Examiner—Yelena Gakh
(74) Attorney, Agent, or Firm—Friedrich Kueffner

(57) ABSTRACT

A method and apparatus for thermally analyzing a sample of a material by detecting a heat flow between the sample and a heat source (1, 2) and, evaluating a functional relation between the measured heat flow and an associated temperature is based on controlling the heating power of the heat source (1, 2) so as to cause the heat source to follow a temperature program ($T_p$) as a function of time superposed with a stochastic variation ($F_{SIP}$), (FIG. 2).

13 Claims, 10 Drawing Sheets

METHOD AND APPARATUS FOR THERMALLY ANALYZING A MATERIAL

BACKGROUND OF THE INVENTION

1. Field of the Invention

The present invention relates to a method for thermally analyzing a material, comprising the steps of providing a sample of said material, providing a heat source so as to cause a flow of heat between said sample and said heat source, controlling a heating condition of said heat source as a function of time, measuring a signal representative of said heat flow between said sample and said heat source and a signal representative of a temperature associated with said heat flow, and evaluating a functional relation between said measured heat flow and temperature signals; and to an apparatus adapted for carrying out said method.

2. Description of the Related Art

In the thermal analysis of materials, a sample of the material is heated by the heat source, and the flow of heat between the heat source and the sample is evaluated to thereby derive structural and compositional information about the material, in particular heat capacity, heat of reaction phase transitions, onset temperatures, etc. In particular, for the sake of accuracy and dynamic range, differential methods, e. g. differential scanning calorimetry (DSC), are being used. In these differential methods, a reference material is arranged in the heat flow symmetrically with respect to the sample to be analyzed, and the analysis is performed on the basis of the differential heat flow between the sample and reference materials.

EP 0 559 362 A1 discloses a differential method wherein the temperature of the heat source is controlled in accordance with a predetermined temperature program so as to cause said heat source temperature to vary in correspondence with a linear rise of temperature superposed by a periodic temperature modulation. A deconvolution technique is used to derive from the differential heat flow signal two separate signal components caused by the linearly changing component and the modulation component of the heat source temperature, respectively.

WO95/33199 and WO95/33200 similarly disclose differential methods wherein a temperature of the heat source is driven through a predetermined temperature program, said temperature program comprising two linearly changing parts of the same time duration in the first case and a linearly changing part superposed by a periodically changing part in the second case. The differential heat flow signal and a phase difference between the differential heat flow signal and the programmed temperature of the heat source are evaluated to separately derive a real and an imaginary signal portion.

In these conventional methods, the thermal excitation of the sample is due to linear or periodic functions, or combinations of both. As a consequence, the subgroup of thermal events which selectively induced by the excitation frequency among the entire group of all possible events. These selectively excited events are those having the same frequency or, depending on the type of excitation and condition of the sample, events corresponding to a multiple integer of the excitation frequency (higher harmonics). The response of the sample is frequency-dependent.

SUMMARY OF THE INVENTION

It is an object of the present invention to provide for a method for thermally analysing a material capable of detecting responses from events without being restricted to frequency-selective excitation. It is a further object to provide for an apparatus which is capable of carrying out this method.

Having regard to the method, this object is attained in accordance with the invention in that said controlling step comprises to stochastically modify said heating condition.

According to the present invention, by stochastically modifying a heating condition, e. g. heating power or heating temperature of the heat source, excitation is not selectively limited to a certain frequency. The response of the material sample depends on how events in the material sample are time-correlated with the excitation. The stochastic excitation allows to directly measure the relaxation function. The relaxation function describes the time response of the material to a pulse-shaped disturbance. The time-dependent excitation of the sample material as opposed to frequency-dependent excitation causes different characteristics and properties of the sample material and the heat transfer path to be detected.

Theoretically, the results of conventional frequency-dependent excitation and stochastic excitation in accordance with the present invention may be mathematically related by means of Fourier transformation. However, this is impossible in practice. To calculate the mathematical relation would require error-free measured values in a frequency and time range between zero and infinity. Since this cannot be realized in practice, the calculation of the mathematical relation suffers loss of information. Moreover, the relation would only apply if the sample material exhibited a linear behaviour during the measurement. However, the assumption of linear behaviour can generally not be made.

The terms "heating", "heat flow", "heat source" and related terms are to be understood in the context of the present specification to mean either heating or cooling. In the latter case, the "heat source" will e. g. be a source of cooling agent thermally coupled to the sample.

In one embodiment of the invention said controlling step is based on a first control input for causing said heat source to assume a predetermined temperature as a function of time and a second control input for stochastically modifying the heating condition of said heat source caused by said first control input.

The second control input for stochastically modifying the heating condition may be defined in terms of a corresponding modification of the temperature, heating rate, heating power or heat flow of the heat source. It may be generated numerically or electronically.

The first control input for causing the heat source to assume a predetermined temperature as a function of time may correspond to the isothermic case where the heating rate is zero and the temperature of the heat source is controlled to be constant at a selected temperature value. In the more general case, the first control input is so that the corresponding temperature-versus-time function varies with time considerably slower than the stochastically varying second control input does. A particularly interesting specific case includes to vary the temperature of the heat source by the first control input in accordance with a linear temperature program, which means a selected constant heating rate.

In another embodiment of the invention, the method further comprises the steps of measuring a temperature of said heat source and using a signal representative of a difference between a superposition of said first control input with said second control input and said measured temperature of said heat source as a heating power control signal for said heat source. In this case, the measured temperature of the heat source is compared with the superposition of the first and second control inputs, and the difference resulting from this comparison is used to control the heating power of the heat source. In this case, the superposed first and second control inputs correspond to the heating temperature of the heat source.

In still another embodiment, the method in accordance with the invention comprises the steps of measuring a temperature of said heat source, filtering said measured temperature of said heat source to thereby derive an average temperature related to the unmodified heating power of said heat source and using a signal representative of a superposition of said second control input with a difference between said first control input and said average temperature as a heating power control signal for said heat source. In this case, the average temperature of the heat source is compared with the first control input, and the second control input is superposed on the result of the comparison to control the heating power of the heat source. Accordingly, the first control input corresponds to the average temperature of the heat source while the second control input causes a stochastic modification of the average temperature corresponding to the first control input.

Preferably, said signal representative of heat flow is a differential signal corresponding to a difference of heat flows between said sample and said heat source and a reference material and said heat source. This provides for high accuracy and wide dynamic range since only the difference in heat flowing into or out of said sample as compared to the heat flowing into or out a known reference material is used for the purposes of analysis, and there is no need for an absolute measurement.

While each of heat source temperature or sample temperature could be used as a temperature associated with the heat flow, it is preferred that a temperature of said reference material is measured and is used as said signal representative of a temperature associated with said heat flow.

According to another essential aspect, the method according to the present invention comprises the steps of deriving an average component of at least one of said measured heat flow and a heating rate derived from said measured temperature associated with said heat flow over a selected interval of time, deriving a dynamical component of at least one of said heat flow and heating rate as a difference between said measured heat flow or derived heating rate, respectively, and said respective derived average component, deriving an average temperature of said measured temperature associated with said heat flow over said selected interval of time and representing at least one of said dynamical components as a function of said derived average temperature.

The dynamical component obtained by this type of evaluation is related to the stochastic variation of the heating power of the heat source while the average component is related to a heating power controlled by the first control input with the stochastic fluctuations caused by the second control input being smoothed out. The length of the time interval selected for the averaging process is dimensioned in accordance with the type of measurement so as to be sufficiently long for obtaining a reasonable average, but not so long as to suppress the excitation responses being looked for in the analysis of the material.

In order to perform the method in accordance with the invention, an apparatus for thermally analyzing a material comprising a heat source, a sample holder having a sample position arranged so as to enable a flow of heat between said heat source and a sample in said sample position, a controller for controlling a heating condition of said heat source as a function of time, means for measuring a signal representative of said heat flow between said sample in said sample position and said heat source, means for measuring a signal representative of a temperature associated with said heat flow and means for evaluating a functional relation between said measured heat flow and temperature signals is in accordance with the invention characterized in that said controller comprises means for stochastically modifying said heating condition. The controller may be implemented by a microcomputer.

In one embodiment, said controller comprises means for setting a first control signal representing a selected temperature program of said heat source as a function of time and means for generating a second control signal stochastically varying in time to thereby stochastically modify said heating condition caused by said first control signal.

Both of the means for setting the first and second control signals may be implemented by means of a microcomputer. In this case, the second control signal may be generated on the basis of a random number generator implemented in the microcomputer. Alternatively, dedicated electronics may be used to generate the second control signal stochastically varying in time.

BRIEF DESCRIPTION OF THE DRAWING

In the following description, the method for thermally analyzing a material in accordance with the invention is exemplarily explained in conjunction with an apparatus adapted for performing the method with reference to the accompanying drawings, in which.

DETAILED DESCRIPTION OF THE PREFERRED EMBODIMENTS

Figure 1:
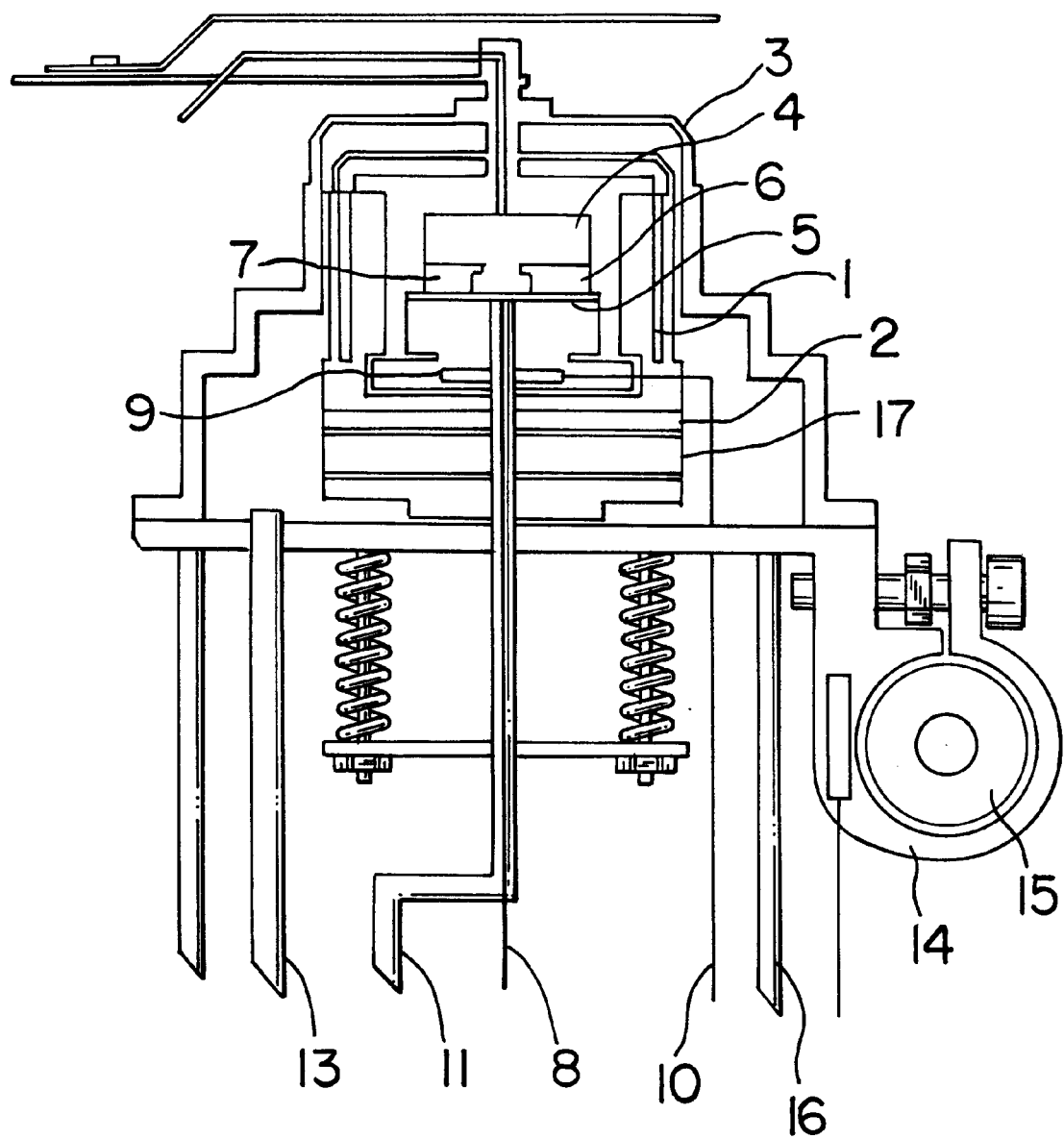
FIG. 1 is a schematic diagram of a major portion of an apparatus for performing the method in accordance with the invention.

As can be seen in FIG. 1, an apparatus for thermally analyzing a material incorporates a heat source comprising an essentially hollow cylindrical oven block 1 made of silver and a flat resistive heater 2 for applying heating power to said oven block 1. Alternatively, a winding of heating wire could be wound onto the exterior cylindrical surface of oven block 1 to provide for resistive heating. A lid assembly 3 on the top end of oven block 1 is automatically movable for opening and closing block 1 to permit access to the interior 4 thereof.

A disc-shaped substrate is arranged in the interior of oven block 1 in thermal contact therewith. Substrate 5 has two circular areas thereof formed as a sample holder and a reference holder, respectively, adapted to support a sample pan 6 and a reference pan 7, respectively. Each of the circular areas of the sample and reference holders are formed with a thermocouple arrangement for detecting a temperature difference between the sample and reference pans 6, 7. The detected temperature difference thus corresponds to a temperature difference between a sample material and a reference material accommodated within the sample and reference pans 6, 7, respectively, in thermal contact therewith. The electrical signal which represents the temperature difference is fed to the outside by means of signal line 8. A platinum thermometer 9 arranged at the bottom portion of oven block 1 detects a temperature of the heat source 1, 2, and a corresponding electrical signal is fed to the outside by signal line 10.

Reference numerals 11, 12 and 13 designate a purge gas supply pipe, purge gas exhaust pipe and dry gas supply pipe, respectively, while reference numerals 14, 15, 16 designate a cooling flange, cooling finger and platinum thermometer; respectively. A heat resistance 17 is provided between the cooling arrangement 14, and the heater 2.

Figure 2:
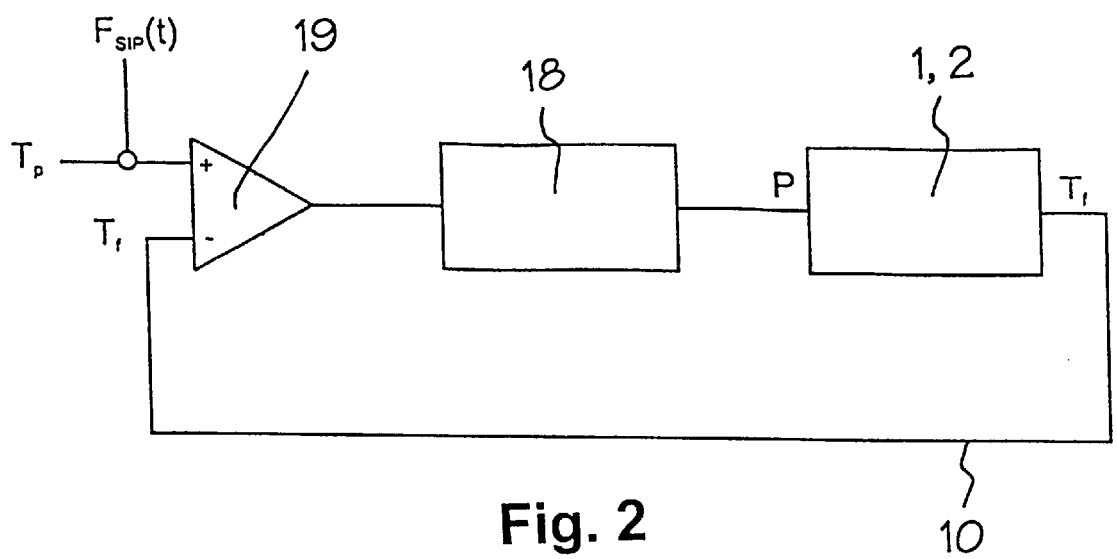
FIG. 2 is a schematic diagram of the control of a heat source in the apparatus of FIG. 1.

Referring to FIG. 2, electrical heating power P is supplied to the heater 2 of heat source 1, 2 by a power controller 18. Power controller 18 controls the amount of heating power P in correspondence with a heating power control signal supplied to a control input thereof from an output of a differential amplifier 19. An inverting input terminal of differential amplifier 19 is supplied with the signal representing the temperature $T_f$ from thermometer 9 on signal line 10. A non-inverting input terminal of differential amplifier 19 has a first control signal $T_p$ and a second control signal $F_{SIP}(t)$ applied thereto. The first control signal $T_p$ is set in a programmer (not shown) so as to drive the heat source 1, 2 through a selected temperature program as a function of time. In particular, the first control signal $T_p$ may set a linear temperature program having a constant heating rate to thereby linearly drive the temperature $T_f$ of the heat source 1, 2 between an initial and final temperature value.

The second control signal $F_{SIP}(t)$ is a stochastic signal which may be numerically generated by a microprocessor or, alternatively, by a hard-wired electronic generator (both not shown). The stochastic second control signal thereby corresponds to a stochastically varying heating rate $\beta_{SIP}(t)$ in accordance with $$F_{SIP}(t) = \int_0^t \beta_{SIP}(t')dt' \quad (1)$$

In this arrangement, the control loop illustrated in FIG. 2 is operative to compare the measured temperature $T_f$ of the heat source 1, 2 with the sum of the temperature $T_p$ set by the first control signal and the stochastical temperature variation $F_{SIP}$ represented by the second control signal to thereby control the heat source temperature $T_f$ accordingly.

Figure 3:
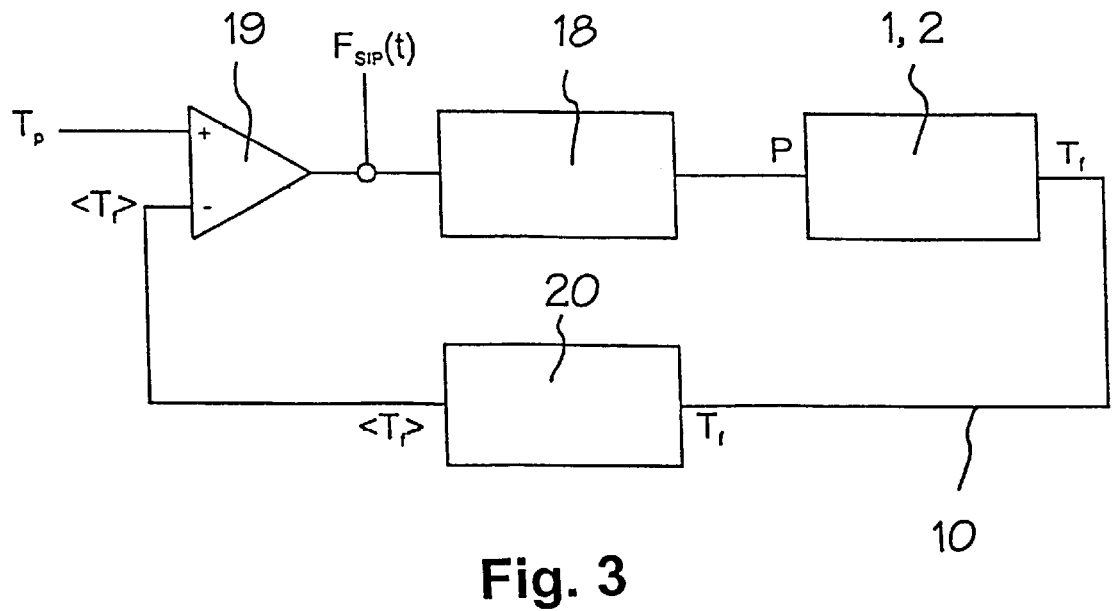
FIG. 3 is a schematic diagram of another embodiment of the control.

The embodiment schematically illustrated in FIG. 3 is a modification of the embodiment of FIG. 2, and identical reference numerals are used for the same parts of FIGS. 2 and 3. FIG. 3 is different from FIG. 2 in two respects: A filter 20 is interposed into signal line 10, and the stochastically varying second control signal $F_{SIP}(t)$ is directly applied to the output signal of differential amplifier 19. Otherwise, FIG. 3 is similar to FIG. 2, and reference is in so far made to the above description of FIG. 2.

Filter 20 is constituted to produce at the output side thereof an average temperature signal $<T_f>$ having the stochastical fluctuations of the heat source temperature $T_f$ caused by the second control signal $F_{SIP}(t)$ smoothed out.

In this arrangement, differential amplifier 19 compares the average temperature $<T_f>$ represented by the average temperature signal with the programmed temperature $T_p$ set by the first control signal, and the stochastically varying second control signal $F_{SIP}(t)$ is superposed on the output signal of differential amplifier 19 to thereby disturb the average temperature value $<T_f>$ of heat source 1, 2 accordingly.

Figure 4:
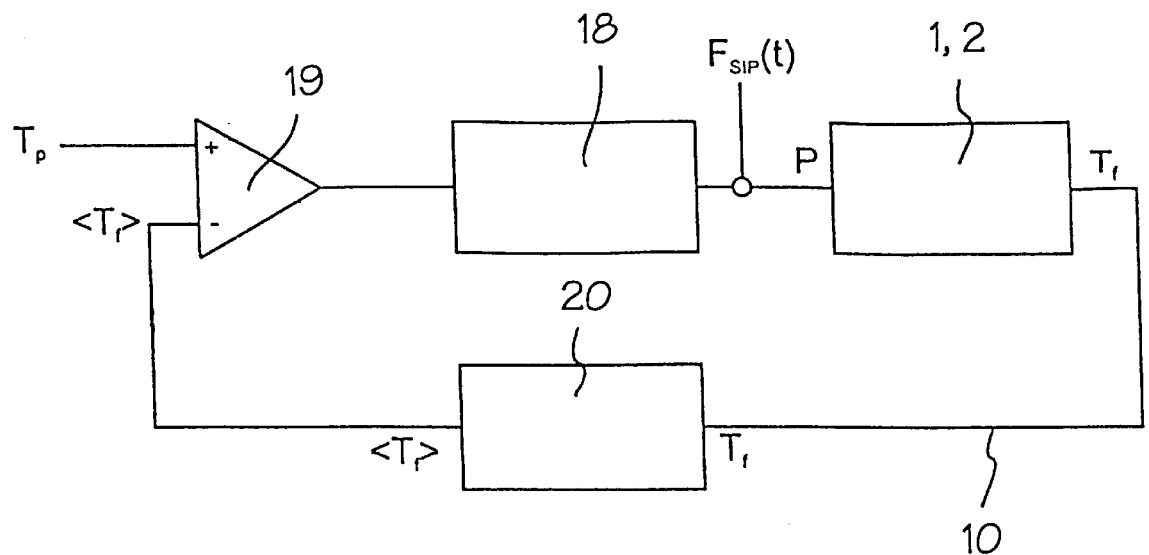
FIG. 4 is a schematic diagram of still another embodiment of the control.

The embodiment of FIG. 4 differs from the one illustrated in FIG. 3 only in that the stochastically varying second control signal $F_{SIP}(t)$ is directly superposed onto the power control output of power controller 18. In this case, the second control signal $F_{SIP}(t)$ is proportional to the stochastically varying heating rate $\beta_{SIP}$.

Figure 5:
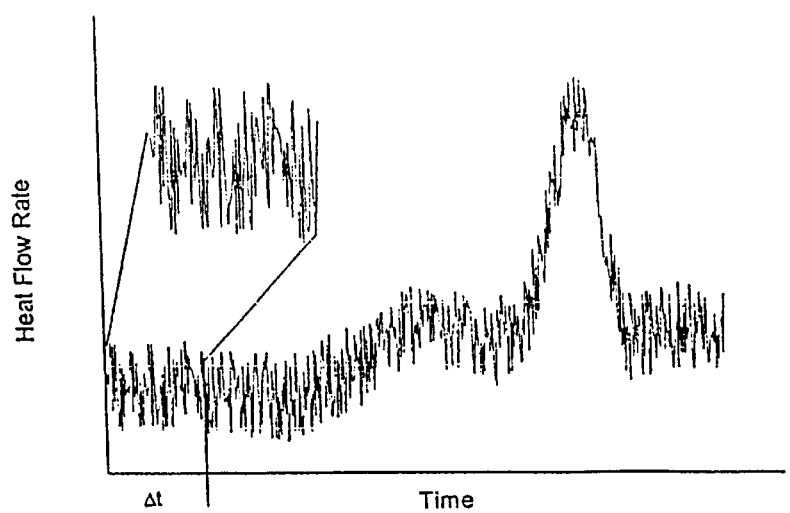
FIG. 5 is a diagram showing a measured signal representing heat flow as a function of time.

As is well-known in conventional calorimetry, the heat flow between sample and heat source is proportional to a difference between sample temperature and heat source temperature, while in the case of a differential method the differential heat flow is proportional to the difference between sample and reference temperatures. The signal on signal line 8 representing the temperature difference between sample and reference in the embodiment of FIG. 1 is thus representative of the differential heat flow $\Phi_m(t)$ where subscript m is to indicate that it is the measured heat flow. This is illustrated in FIG. 5 showing the heat flow $\Phi_m(t)$ as a function of time with a portion covering a time interval $\Delta t$ additionally illustrated at an enlarged scale. To evaluate a functional relation between the heat flow $\Phi_m(t)$ and temperature and to discriminate between a dynamical component related to the stochastic variations and an average component related to an average temperature, an analysis of the measured signals including averaging has to be performed. This analysis can be made in terms of either one of the sample or reference temperatures as detected by the thermocouples located at the sample and reference pans 6, 7 in FIG. 1 or, alternatively, in terms of the heat source temperature $T_f$ as detected by thermometer 9 in FIG. 1. Any difference in using the three before-referenced temperature values may be taken into account by calibration.

One useful way of analysis is to calculate autocorrelation functions a $\alpha_{\Phi\Phi}(t)$, $\alpha_{\beta\beta}(t)$ and cross-correlation functions $\alpha_{\Phi\beta}(t)$ for the measured heat flow and heating rate (which is the time derivative of the measured temperature) for a suitably selected time interval $\Delta t$ in accordance with $$\alpha_{\Phi\Phi}(t, T_n) = \frac{1}{\Delta t}\int_{t_n}^{t_n+\Delta t} \Phi_m(t')\Phi_m(t'+t)dt' \quad (2)$$

$$\alpha_{\beta\beta}(t, T_n) = \frac{1}{\Delta t}\int_{t_n}^{t_n+\Delta t} \beta(t')\beta(t'+t)dt' \quad (3)$$

$$\alpha_{\Phi\beta}(t, T_n) = \frac{1}{\Delta t}\int_{t_n}^{t_n+\Delta t} \Phi_m(t')\beta(t'+t)dt' \quad (4)$$

where $t_n$ is selected from the set of N points of time where measured values are taken. This leads to a maximum of N auto- and cross-correlation functions. The temperature $T_n$ associated with the auto- and cross-correlation functions of equations (2) to (4) is the average temperature over the time interval $\Delta t$ according to $$T_n = \frac{1}{\Delta t}\int_{t_n}^{t_n+\Delta t} T(t')dt' \quad (5)$$

By means of the above auto- and cross-correlation functions, average values $\Phi_0$ and $\beta_0$ may be obtained for the heat flow and heating rate, respectively, by a limes operation in accordance with $$\alpha_{\beta\beta}(t\to\infty, T_n)=(\beta_0(T_n))^2$$

$$\alpha_{\Phi\beta}(t\to\infty, T_n)=\Phi_0(T_n)\beta_0(T_n)$$

$$\alpha_{\Phi\Phi}(t\to\infty, T_n)=(\Phi_0(T_n))^2 \quad (6)$$

The infinity limes in equation (6) above has to be understood to mean a suitably long time interval $\Delta t$. Further, it has to be understood that no thermal event of the sample should fall into a time interval $\Delta t$ at the start of the measurement.

The above limes calculation therefore allows to determine the average values $\Phi_0$ and $\beta_0$ for heating rate and heat flow. This could alternatively also be determined by averaging in accordance with $$\Phi_0(T_n) = \frac{1}{\Delta t}\int_{t_n}^{t_n+\Delta t}\Phi_m(t')dt' \quad (7)$$

Thereby the length of the time interval $\Delta t$ may be optimally selected for each portion of the total length of the measured curve. The length of the time interval $\Delta t$ may be dependent on the characteristics of the sample. In portions where there are no or only minor variations in the average heat flow, the time interval $\Delta t$ may be selected larger than in portions where a relatively fast thermal event occurs.

The dynamical components are obtained by subtracting the average components in accordance with $$\alpha_{\beta\beta}^d(t,T_n)=\alpha_{\beta\beta}(t,T_n)-\beta_0^2 \quad (8)$$

$$\alpha_{\Phi\Phi}^d(t,T_n)=\alpha_{\Phi\Phi}(t,T_n)-\Phi_u(T_n)^2 \quad (9)$$

$$\alpha_{\Phi\beta}^d(t,T_n)=\alpha_{\Phi\beta}(t,T_n)-\Phi_u(T_n)\beta_0 \quad (10)$$

Figure 6:
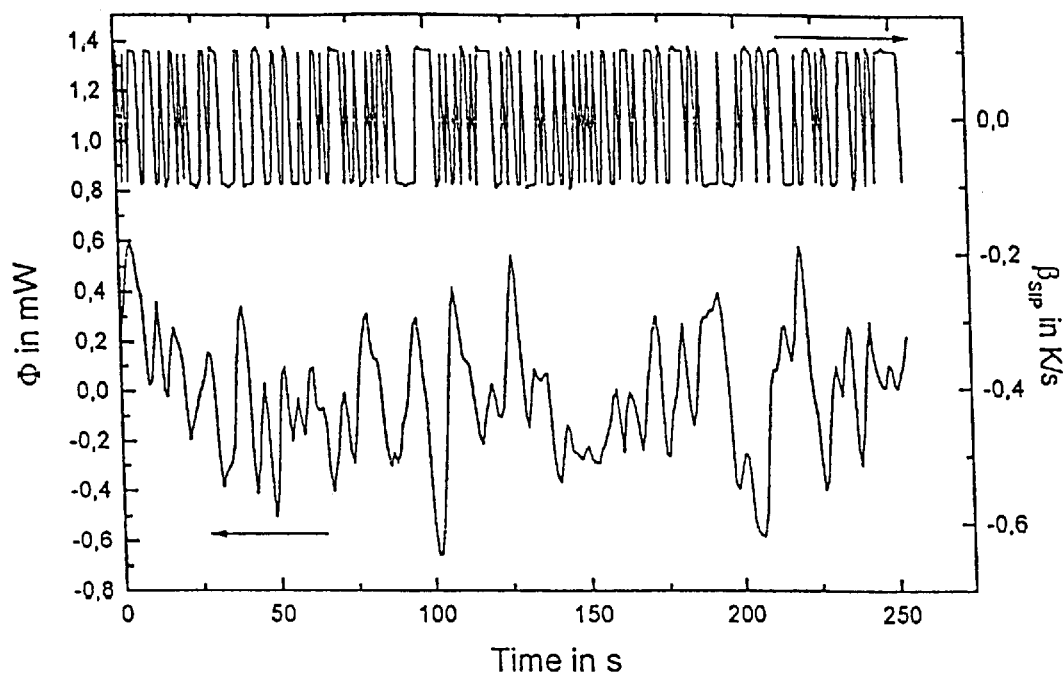
FIG. 6 is a diagram showing each of a dynamical component of heat flow and heating rate as a function of time.

FIG. 6 illustrates the dynamical components of heat flow and heating rate caused by the stochastically varying excitation in polystyrene at a temperature of 350 K.

Figure 7:
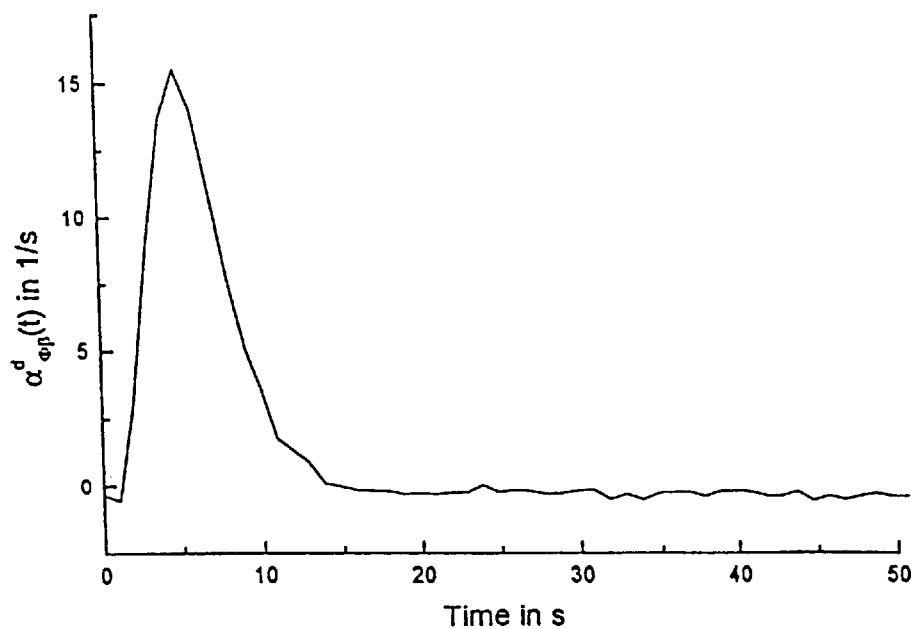
FIG. 7 is a diagram showing a non-corrected relaxation function.

$\alpha_{\Phi\beta}^d(t,T_n)$ as defined in equation (10) is the non-corrected relaxation function. This function characterizes the sample and the heat transfer path. FIG. 7 illustrates the non-corrected relaxation function calculated from the dynamical components in FIG. 6.

A corrected relaxation function is obtained by calibration. A calibration function g(t) may be obtained from the correlation functions measured at a temperature where thermal events do not occur (e. g. at the start of the measurement) and the dynamical component $\alpha_{\beta\beta}^d(t,T_n)$ of the heating rate auto-correlation function. The corrected relaxation functions of the sample $\rho(t,T_n)$ can be calculated from the convolution $$\rho(t, T_n) = \int_0^{\Delta t} g(t-t', T_n)\alpha_{\Phi\beta}^d(t', T_n)dt' \quad (11)$$

From a physical point of view, knowledge of the relaxation function for all temperatures is sufficient and powerful information. It is excellently appropriate to verify physical models through time-dependent processes and to obtain information concerning the dynamical behaviour of the sample. Such comprehensive information cannot be obtained from frequency-dependent analysis even if a plurality of frequencies is used.

If the corrected relaxation function of the sample is known and the non-corrected relaxation is determined, a calibration function can be determined. Using this function, the heat transfer behaviour of the sample or the calorimeter may be characterized.

Another alternative of evaluation is Fourier transformation. For this purpose, the stochastically varying dynamical component $\Phi_s$ has at the outset to be separated by filtering or any other averaging procedure. In each measured time interval of length $\Delta t$, the dynamical component of heat flow is related to the dynamical component of heating rate according to $$\Phi_s(t, T_n) = \int_{t_n}^{t_n+\Delta t} \alpha_{\Phi\beta}^d(t-t', T_n)\beta_{SIP}(t', T_n)dt' \quad (12)$$

The above convolution integral may e. g. be solved by calculating the Fourier transforms $\Phi_s^\omega(\omega, T_n)$ and $\beta_{SIP}^\omega(\omega, T_n)$ of $\Phi_s(t, T_n)$ and $\beta_{SIP}(t, T_n)$, respectively. This yields the non-calibrated complex heat capacity $C_m^*$ in accordance with $$C_m^*(\omega, T_n) = \frac{\Phi_s^\omega(\omega, T_n)}{\beta_{SIP}^\omega(\omega, T_n)} \quad (13)$$

Figure 8:
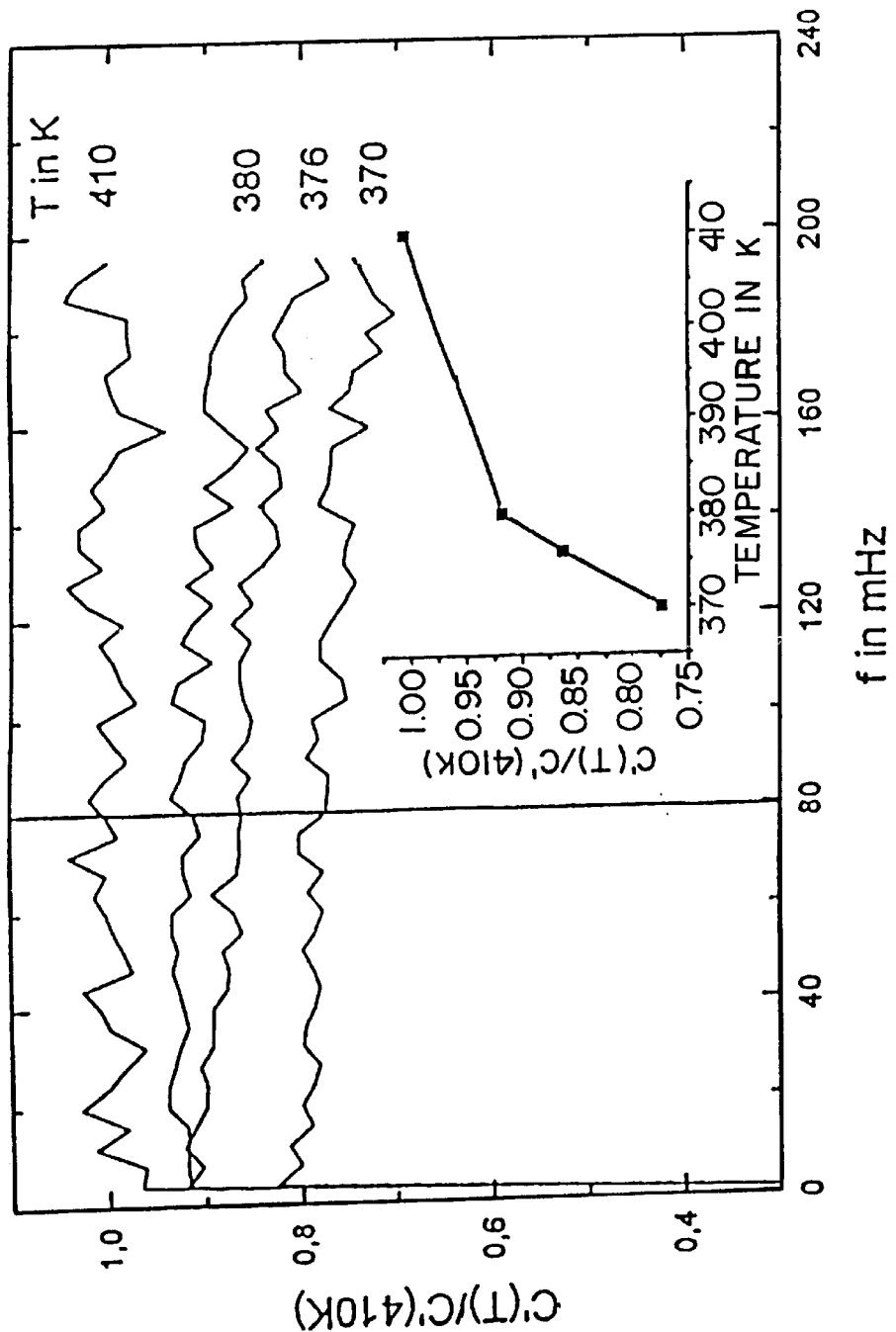
FIG. 8 is a diagram showing a real part of the complex heat capacity of polystyrene at different temperatures in the glass transition region.

After calibration, curves as illustrated in FIG. 8 are obtained. FIG. 8 shows the normalized real part of the complex heat capacity of polystyrene at various temperatures in the glass transition region. The small diagram inserted in the illustration of FIG. 8 shows for 80 mHz the temperature dependency obtained from the measured curves.

Another way of evaluation is to use narrow band pass filters to thereby extract individual pieces of information from the measured curve which allow to derive frequency-dependent parameters.

A still further way is to develop a model of the measuring apparatus. This model leads to differential equations for the heat flow within the apparatus. In addition, a model for the physical and chemical behaviour of the sample is developed. The equations obtained are combined with those of the measuring apparatus. As a solution of the differential equations, equations are obtained which contain parameters describing the measuring apparatus and parameters describing the sample. The parameters characterizing the measuring apparatus may be determined experimentally, and the measured heat flow $\Phi_m$ or, alternatively, the stochastically varying dynamical component $\Phi_s$ thereof may be fitted with the model equations using the dynamical heating rate $\beta_{SIP}$. This yields the parameters which characterize the sample.

Figure 9:
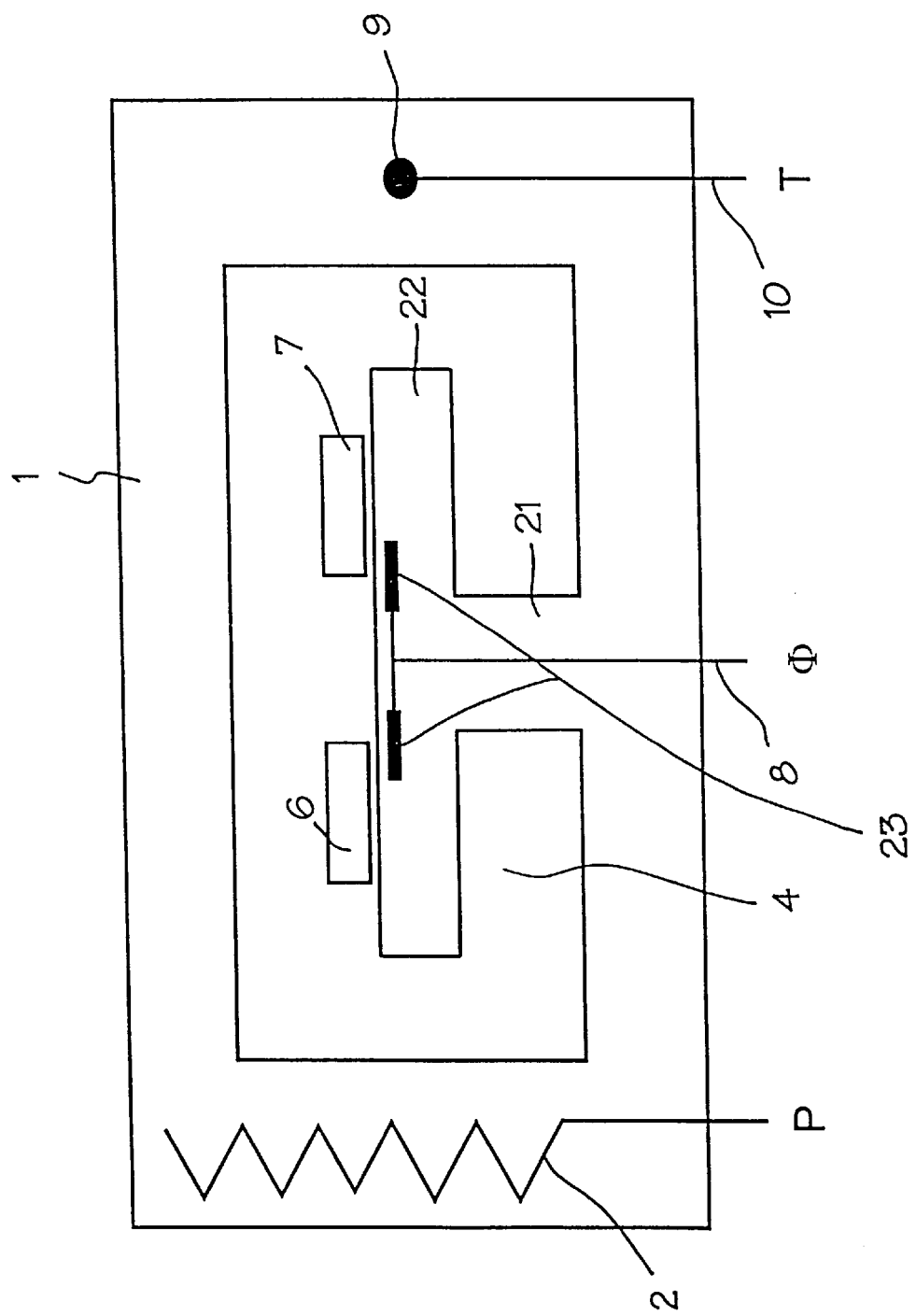
FIGS. 9 to 13 show various modified forms of the apparatus of FIG. 1.

There is a wide variety of arrangements to implement the stochastic modifications of heating conditions. FIG. 9 schematically illustrates an apparatus essentially similar to the one shown in FIG. 1. The same reference numerals are used for those elements which correspond to the elements of FIG. 1. In the arrangement of FIG. 9, a flow path member 21 integrally formed with oven block 1 projects into the interior 4 of oven block 1. An end portion 22 of flow path member 21 is of a disk-like shape to support the sample and reference pans 6, 7, respectively. Flow path member 21 is of the same thermally conductive material as oven block 1 causing the thermal coupling between oven block 1 and sample or reference pan 6, 7, respectively, to be relatively strong.

Thermocouple arrangement 23 provided at end portion 22 at locations close to said sample and reference pans 6, 7 detects a temperature difference between the sample and reference pans 6, 7. A signal corresponding to the detected temperature difference is fed to the outside by signal line 8, and this differential temperature signal is representative of the differential heat flow Φ. The signal from platinum thermometer 9 in oven block 1 is representative of oven temperature T.

The apparatus may be controlled according to one of the methods illustrated and described with reference to FIGS. 2 to 4 above. As an alternative, the heating power (cooling power) of heater (cooler) 2 may be controlled in accordance with $P=P_0(t)+F_{SIP}(t)$ where $P_0$ may be constant or may vary in accordance with a non-stochastic time program while temperature T and differential heat flow Φ are measured and evaluated.

In another alternative, the differential heat flow may be given as a stochastic function and the heating power is correspondingly controlled while the temperature T is measured.

Figure 10:
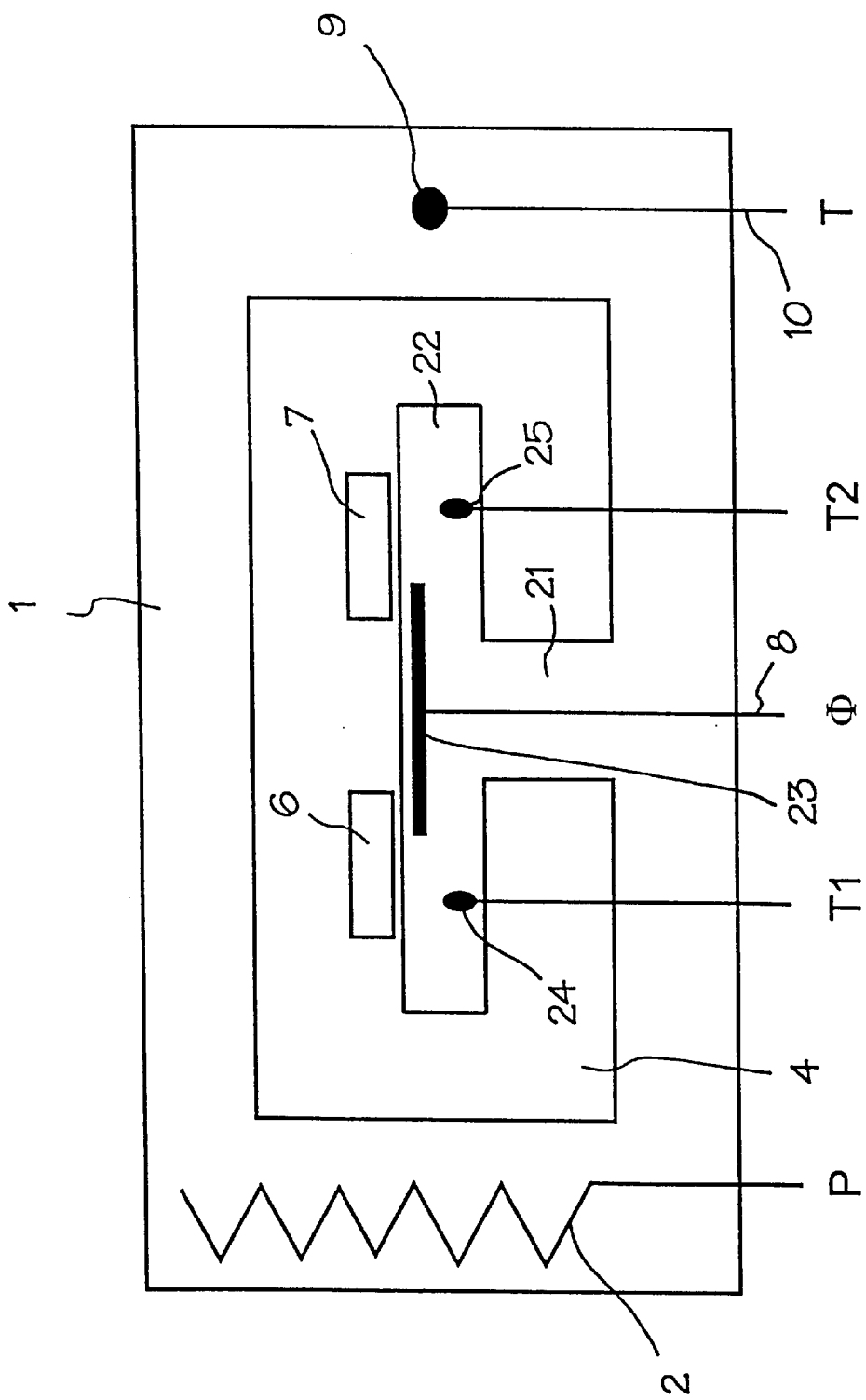

The arrangement illustrated in FIG. 10 corresponds to the one illustrated in FIG. 9, and the same elements are designated with the same reference numerals. In FIG. 10, end portion 22 of flow path member 21 is provided with additional temperature sensors for detecting a temperature $T_1$ and $T_2$ at locations close to the sample and reference pans 6, 7, respectively.

The alternative ways of controlling the apparatus of FIG. 9 may also be used for the apparatus illustrated in FIG. 10. In this case, any of the temperatures $T_1$, $T_2$ or a sum of these temperatures may be used instead of the temperature T which is used as the control variable or measured variable in the alternatives of FIG. 9.

Figure 11:
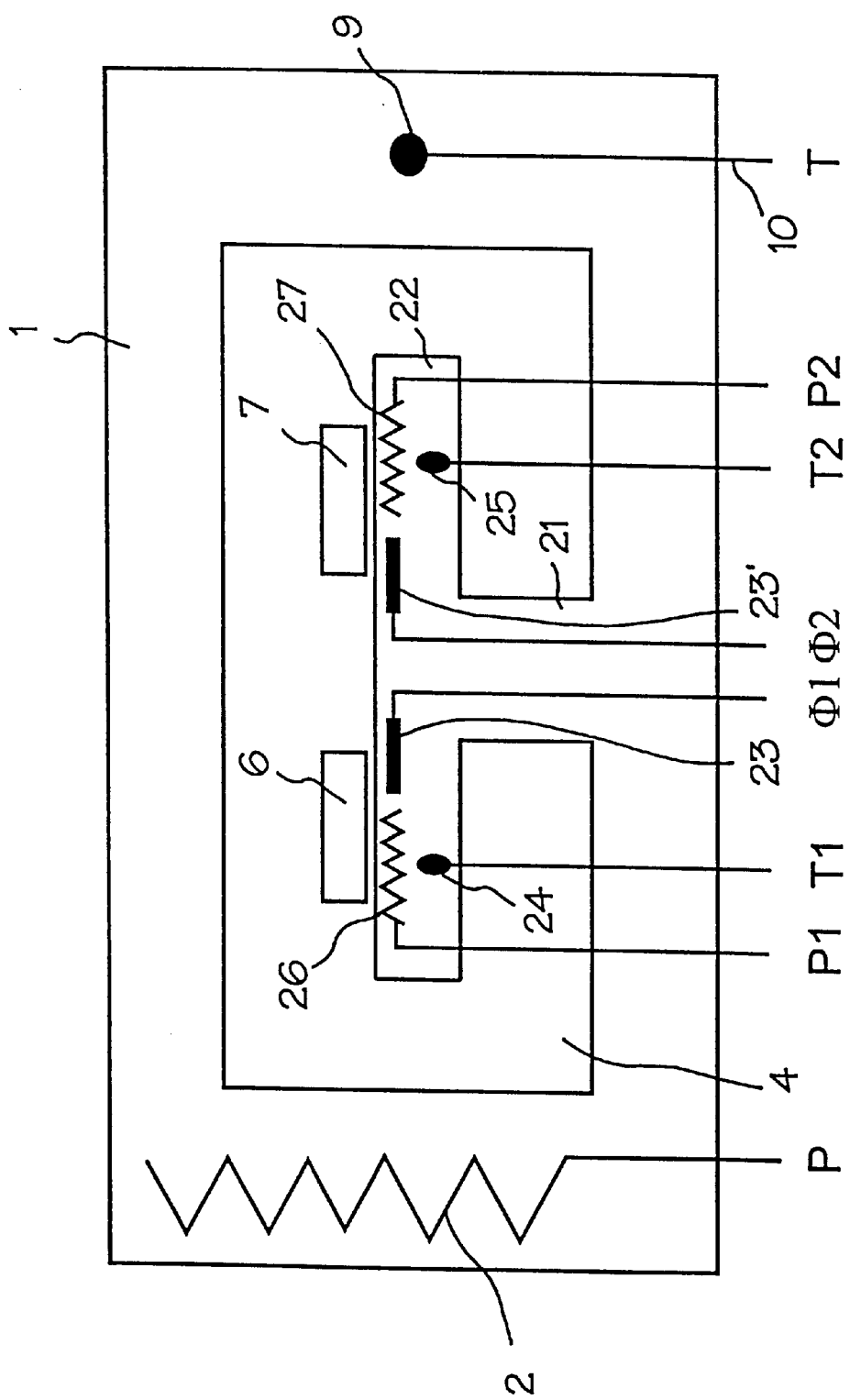

The arrangement illustrated in FIG. 11 incorporates all elements of the one illustrated in FIG. 10 as indicated by the same reference numerals. In the embodiment of FIG. 11, heater 2 serves as a first heating device to provide for non-stochastic basic heating only. In addition, second heating devices 26, 27 for stochastically modifying the basic heating are arranged at end portion 22 of flow path member 21 at locations close to the sample and reference pans 6, 7, respectively. The stochastic heating powers applied by the second heating devices 26, 27 are designated as P1 and P2, respectively. Further, separate thermocouple arrangements 23, 23' are provided in FIG. 11 for the sample and reference pans 6, 7. In this way, the heat flows Φ1 and Φ2 relating to the sample and reference pans may be detected and controlled separately. Any of the control methods described above with reference to FIGS. 9 or 10 may be used.

Figure 12:
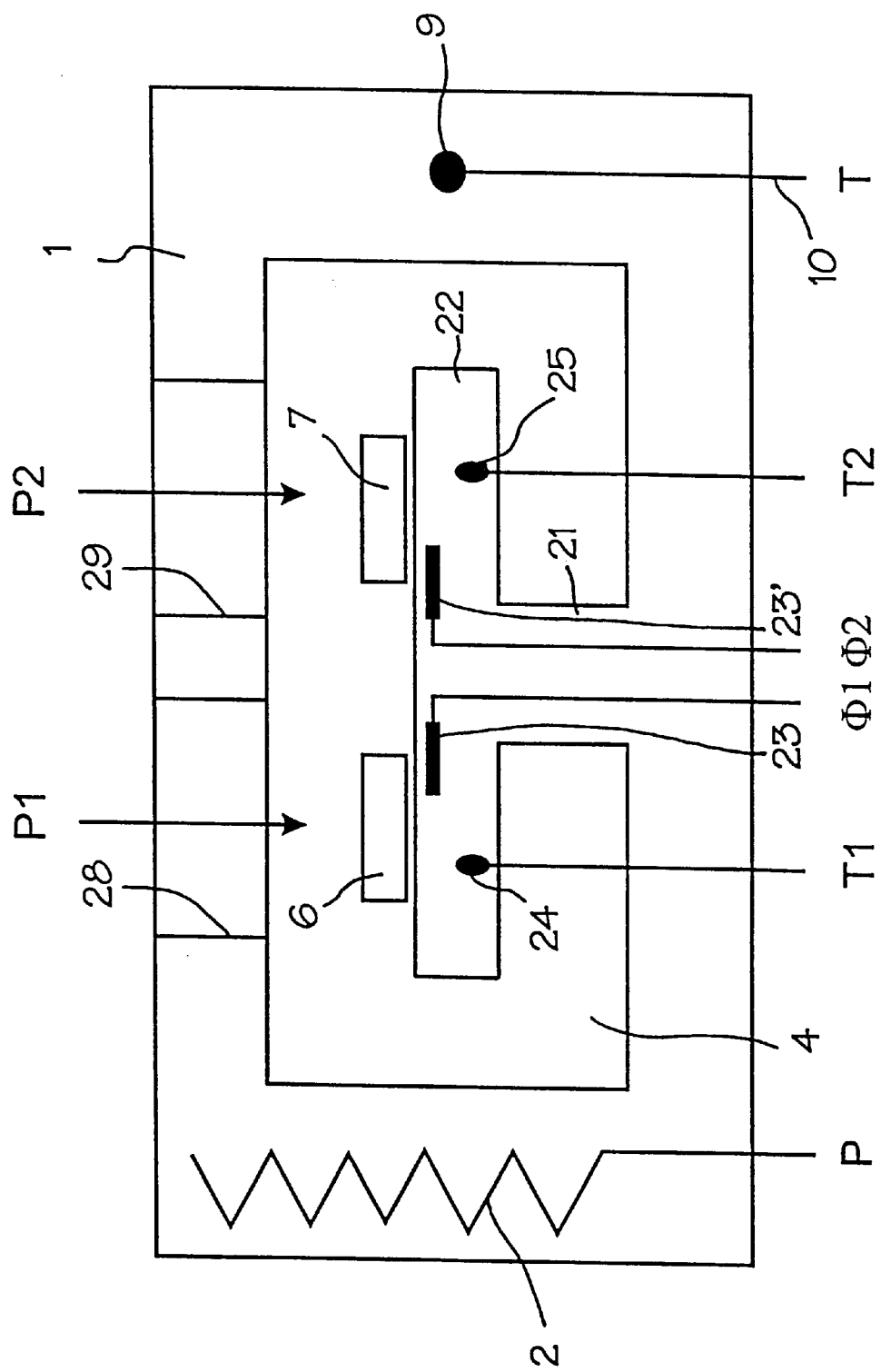

The embodiment of FIG. 12 uses radiation sources for the second heating devices instead of the resistive heaters 26, 27 of FIG. 11. Windows 28, 29 aligned with the sample and reference pans 6, 7, respectively, are formed in oven block 1 to enable these radiation sources to irradiate stochastically varying heating power P1, P2 onto the sample and reference pans 6, 7.

Figure 13:
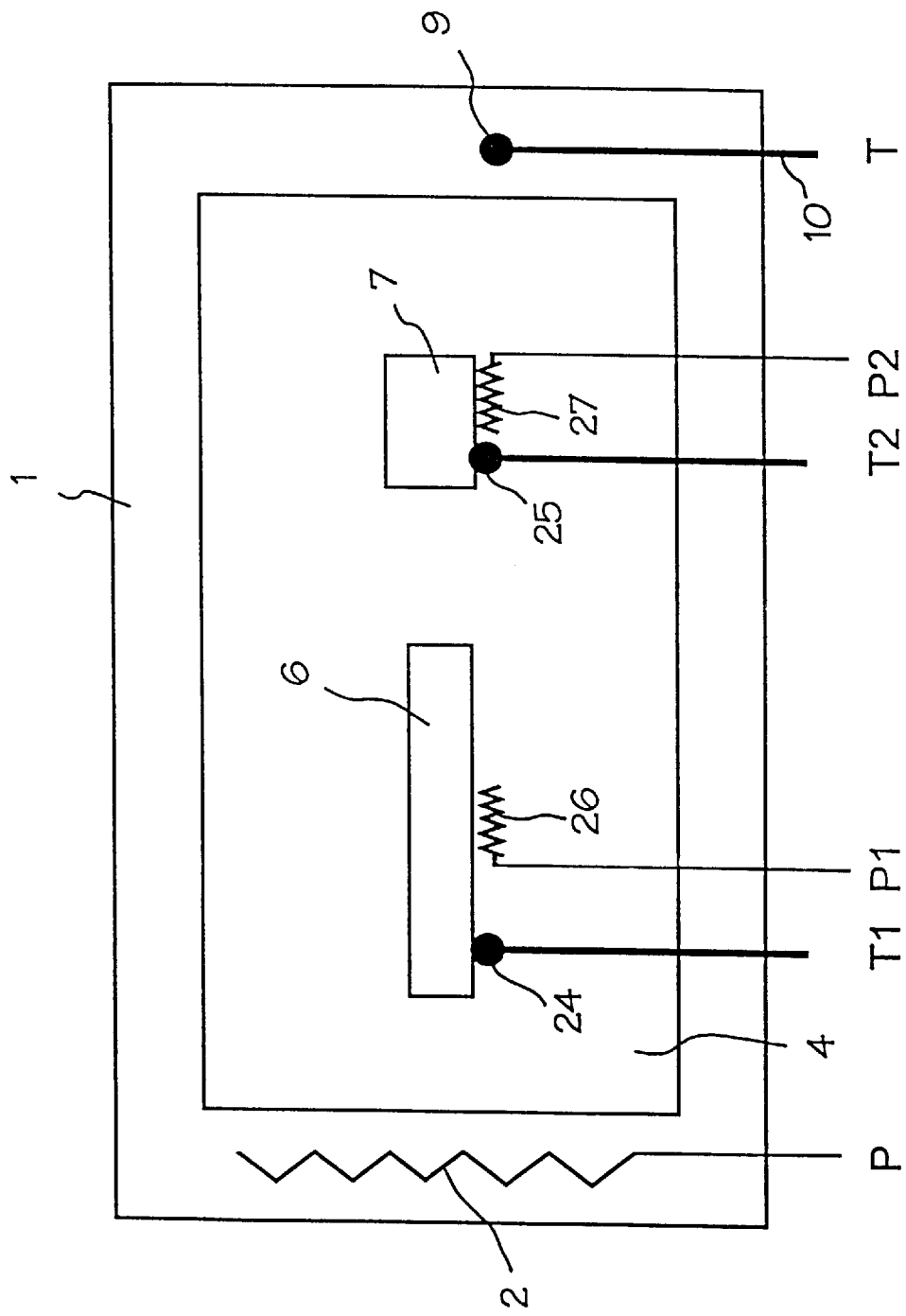

In the arrangements illustrated in FIGS. 9 to 12, the flow path member 21 is used to conduct the heat flow, and this results in strong thermal coupling of the sample and reference to the heat source. As opposed to this, the arrangement of FIG. 13 uses only weak thermal coupling of sample 6 and reference 7 to oven block 1 via the atmosphere in the interior 4 of oven block 1. The temperature T of oven block 1 is maintained at a desired temperature program by controlling the heating power P of heater 2 accordingly. The second heating devices 26, 17 provide for stochastic heating. The temperatures T1 and T2 from temperature sensors 24, 25 may be predetermined to vary stochastically while the necessary heating powers P1 and P2 from the second heating devices 26, 27 may be measured and evaluated. Alternatively, P1 and P2 may be the stochastically varying control variables while the temperatures T1 and T2 or a combination thereof may be measured and evaluated.

Various other modifications may be applied. In particular, radiation sources similar to FIG. 12 could be used for the second heating devices 26, 27 instead of the resistive heaters in FIG. 13.

LIST OF REFERENCE NUMERALS 1 oven block
2 heater
3 lid assembly
4 interior
5 substrate
6 sample pan
7 reference pan
8 signal line
9 thermometer
10 signal line
11 purge gas supply pipe
12 purge gas exhaust pipe
13 dry gas supply pipe
14 cooling flange
15 cooling finger
16 platinum thermometer
17 heat resistance
18 power controller
19 differential amplifier
20 filter
21 flow path member
22 end portion
23, 23' thermocouple arrangement
24, 25 temperature sensors
26, 27 second heating devices
28, 29 windows

What is claimed is:

1. A method for thermally analyzing a material, comprising the steps of:
   providing a sample of said material;
   providing a heat source so as to cause a flow of heat between said sample and said heat source;
   controlling a heating condition of said heat source as a function of time;
   measuring a signal representative of said heat flow between said sample and said heat source and a signal representative of a temperature associated with said heat flow; and
   evaluating a functional relation between said measured heat flow and temperature signals, wherein said controlling step comprises stochastically modifying said heating condition.

2. A method according to claim 1, wherein said controlling step is based on a first signal input for causing said heat source to assume a predetermined temperature as a function of time and a second signal input for stochastically modifying the heating condition of said heat source caused by said first control input.

3. A method according to claim 2, further comprising the steps of measuring a temperature signal of said heat source; and using a signal representative of a difference between a superposition of said first signal input with said second signal input and said measured temperature signal of said heat source as a heating power control signal for said heat source.

4. A method according to claim 2, further comprising the steps of measuring a temperature of said heat source;

filtering said measured temperature signal of said heat source to thereby receive an average temperature related to the unmodified heating power of said heat source; and using a signal representative of a superposition of said second control input with a difference between said first signal and said average temperature as a heating power control signal for said heat source.

5. A method according to claim 1, wherein said signal representative of heat flow is a differential signal corresponding to a difference of heat flows between said sample and said heat source and a reference material and said heat source.

6. A method according to claim 5, wherein a temperature of said reference material is measured and is used as said signal representative of a temperature associated with said heat flow.

7. A method according to claim 1, wherein said step of evaluating a functional relation between said measured heat flow and temperature signals comprises the steps of deriving an average component of at least one of said measured heat flow and a heating rate derived from said measured temperature associated with said heat flow over a selected interval of time;

deriving a dynamical component of at least one of said heat flow and heating rate as a difference between said measured heat flow or derived heating rate, respectively, and said respective derived average component;

deriving an average temperature of said measured temperature associated with said heat flow over said selected interval of time; and representing at least one of said dynamical components as a function of said derived average temperature.

8. A method according to claim 7, wherein said step of deriving an average component of at least one of said measured heat flow and heating rate derived from said measured temperature associated with said heat flow comprises calculating at least one of an autocorrelation function or cross-correlation function of said heat flow and heating rate, and said at least one of said dynamical components is calculated as a difference between a respective one of said autocorrelation or cross-correlation functions and a limes value of said autocorrelation or cross-correlation functions.

9. A method according to claim 8, further comprising the step of calculating a calibration function on the basis of at least one of said correlation functions corresponding to a selected time interval where there is no thermal event in said material.

10. A method according to claim 9, wherein at least one relaxation function of said material is calculated as a convolution integral of said calibration function and at least one of said correlation functions.

11. A method according to claim 1 wherein said derived dynamical components of heat flow and heating rate are further evaluated by means of Fourier transformation.

12. A method according to claim 7, wherein at least one of said dynamical components is derived by filtering.

13. A method according to claim 7, wherein at least one of said dynamical components is derived from model equations describing the behaviour of said heat source and of a heat flow path between said sample and said heat source.

* * * * *